US010527596B2

(12) United States Patent
Takasu

(10) Patent No.: US 10,527,596 B2
(45) Date of Patent: Jan. 7, 2020

(54) CALCULATION DEVICE AND CALCULATION METHOD

(71) Applicant: FUJITSU LIMITED, Kawasaki-shi, Kanagawa (JP)

(72) Inventor: Ryozo Takasu, Isehara (JP)

(73) Assignee: FUJITSU LIMITED, Kawasaki (JP)

( * ) Notice: Subject to any disclaimer, the term of this patent is extended or adjusted under 35 U.S.C. 154(b) by 690 days.

(21) Appl. No.: 15/232,340

(22) Filed: Aug. 9, 2016

(65) Prior Publication Data

US 2017/0153213 A1 Jun. 1, 2017

(30) Foreign Application Priority Data

Nov. 26, 2015 (JP) ................................ 2015-230843

(51) Int. Cl.
*G01N 33/00* (2006.01)
*G01N 15/02* (2006.01)

(52) U.S. Cl.
CPC ..... *G01N 33/0027* (2013.01); *G01N 33/0062* (2013.01); *G01N 15/02* (2013.01)

(58) Field of Classification Search
CPC ........... G01N 33/0027; G01N 33/0062; G01N 15/02; G01N 15/0062; G01N 2015/0046; G01N 2015/0693
See application file for complete search history.

(56) References Cited

U.S. PATENT DOCUMENTS 8,706,424 B2 * 4/2014 Stephens .............. G01N 33/005 123/672
9,594,037 B2 * 3/2017 Mizuno ..................... G01T 7/04
(Continued)

FOREIGN PATENT DOCUMENTS

CN 101354332 1/2009
CN 103245637 8/2013
(Continued)

OTHER PUBLICATIONS

Arling, "Air Quality Sensor Network for Philadelphia—Data Validation-", 2010.*

(Continued)

*Primary Examiner* — Mohamed Charioui
*Assistant Examiner* — Catherine T. Rastovski
(74) *Attorney, Agent, or Firm* — Fujitsu Patent Center

(57) ABSTRACT

A calculation device includes: an acquisition unit that obtains a mass concentration of particles in a gas measured in a first measurement station, a number concentration of particles in the gas measured in a second measurement station, and a humidity of the gas measured in the second measurement station; and a calculation unit that calculates a function, which defines a relationship of a mass concentration and a number concentration to a humidity and is used to calculate a mass concentration of particles in the gas in a third measurement station from a number concentration of particles in the gas and a humidity of the gas measured in the third measurement station, based on the mass concentration in the first measurement station and the number concentration and the humidity in the second measurement station, the third measurement station being installed in a different location from the first and second measurement stations.

14 Claims, 12 Drawing Sheets

(56) References Cited

U.S. PATENT DOCUMENTS

| | | | | |
|---|---|---|---|---|
| 9,726,579 | B2 * | 8/2017 | Han | G01N 1/2205 |
| 2017/0248494 | A1 * | 8/2017 | Miller | G01N 15/02 |

FOREIGN PATENT DOCUMENTS

| | | |
|---|---|---|
| CN | 104122180 | * 10/2014 |
| JP | 2001-343319 | 12/2001 |
| JP | 2014-228309 | 12/2014 |
| JP | 2014-240733 | 12/2014 |

OTHER PUBLICATIONS

CNOA—Office Action of Chinese Patent Application No. 201610827459.8 dated Feb. 20, 2019, with full English translation of the Office Action.

JPOA—Office Action of Japanese Patent Application No. 2015-230843 dated Jun. 11, 2019, with full English translation of the Office Action.

Takasu et al.,"Construction and application of an atmospheric environment monitoring system using a simple type PM 2.5 measuring device", a summary of the oral environment society, Aug. 31, 2014, vol. 55th, p. 330. cited in JP-OA dated Jun. 11, 2019 for corresponding Japanese Application No. 2015-230843.

* cited by examiner

CALCULATION DEVICE AND CALCULATION METHOD

CROSS-REFERENCE TO RELATED APPLICATION

This application is based upon and claims the benefit of priority of the prior Japanese Patent Application No. 2015-230843, filed on Nov. 26, 2015, the entire contents of which are incorporated herein by reference.

FIELD

A certain aspect of embodiments described herein relates to a calculation device and a calculation method.

BACKGROUND

In recent years, the level of particulate matters such as $PM_{2.5}$ in the air has actively been measured. The concentration of particles in a gas is represented by a mass of particles contained in a gas of unit volume (for example, $mg/m^3$ or $\mu g/m^3$). This particle concentration is called a mass concentration. One of classic techniques for measuring the mass concentration of $PM_{2.5}$ traps particles in a gas on a filter, and then measures the mass of the trapped particles. Alternatively, a beta attenuation measurement has been known as a technique that can measure a mass concentration automatically. The concentration obtained through the filter technique or the beta attenuation measurement is a mass concentration. Thus, the concentration of $PM_{2.5}$ is currently normally indicated by the mass concentration. Furthermore, as a simple method, there is a light scattering detecting method that illuminates particles in a gas and then measures the number of particles contained in a gas of unit volume (e.g., the number of particles/$m^2$) with the scattered light. There has been known several methods of automatically measuring the concentration of particles in the air as disclosed in Japanese Patent Application Publication Nos. 2001-343319, 2014-240733, and 2014-228309.

SUMMARY

According to an aspect of the present invention, there is provided a calculation device including: an acquisition unit configured to obtain a mass concentration of particles contained in a gas measured in a first measurement station, a number concentration of particles contained in the gas measured in a second measurement station, and a humidity of the gas measured in the second measurement station; and a calculation unit configured to calculate a function, which defines a relationship of a mass concentration and a number concentration to a humidity and is used to calculate a mass concentration of particles contained in the gas in a third measurement station from a number concentration of particles contained in the gas and a humidity of the gas measured in the third measurement station, based on the mass concentration in the first measurement station and the number concentration and the humidity in the second measurement station obtained by the acquisition unit, the third measurement station being installed in a location different from a location where the first measurement station and the second measurement station are installed.

DESCRIPTION OF EMBODIMENTS

Figure 1:
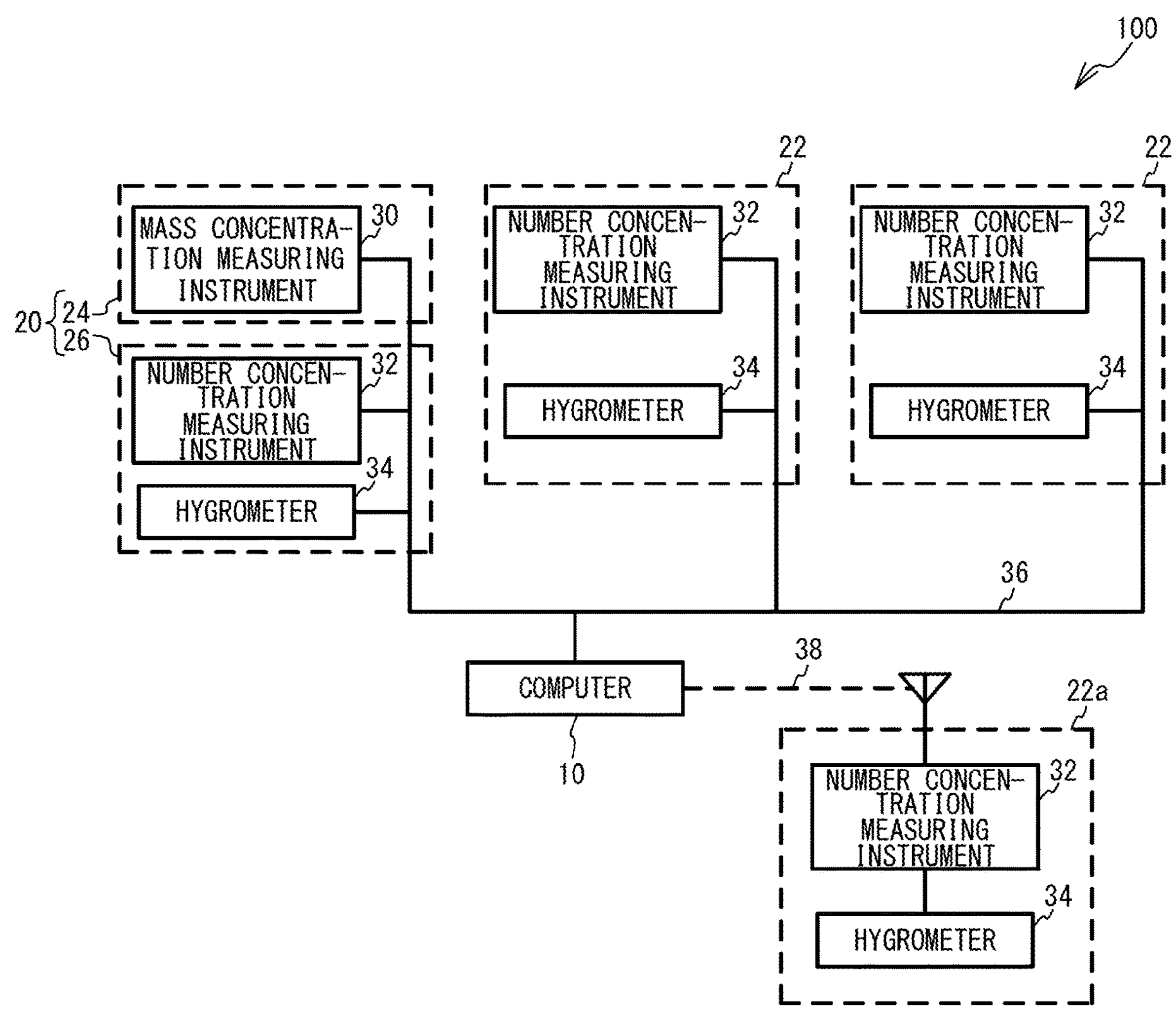
FIG. 1 is a block diagram of a system that employs a calculation device and a calculation program in accordance with a first embodiment.

The technique that traps particles on a filter needs, for example, 24 hours or more for each measurement. In addition, automatic measurement is difficult. The beta attenuation measurement can automatically measure a mass concentration. However, its measurement time is not sufficiently short. In addition, the measuring device is large and expensive. Thus, it is difficult to install many measurement stations each being equipped with a mass concentration detector.

It has been also desired to obtain information on the composition of particles by a simple technique.

The demand for more frequent measurement of $PM_{2.5}$ has increased because of the effect of $PM_{2.5}$ or other particulate matters on health. However, the number of measurement stations for measuring the concentration of $PM_{2.5}$ is below 1000 across the country. In addition, the distribution of the installed locations is uneven. Thus, the above demand is not sufficiently fulfilled.

If closely located measurement stations collect and deliver data on concentrations of $PM_{2.5}$ in real time, the data is helpful in taking measures when the rise in the concentration of $PM_{2.5}$ is expected. In addition, the data will contribute to the prediction of $PM_{2.5}$ concentration, the identification of source of $PM_{2.5}$, and/or atmospheric science simulations.

Mass concentration measuring instruments employing the technique that traps particles on a filter or the beta attenuation measurement are expensive. Thus, it is difficult to install measurement stations equipped with a mass concentration detector all over the country. In addition, since the measuring time is long, real-time measurement is difficult.

In contrast, number concentration measuring instruments employing the light scattering detection method can automatically measure a number concentration, and is less expensive. Thus, measurement stations equipped with the number concentration measuring instrument may be installed all over the country. Such an installation allows data on the concentration of particles in each area to be aggregated in real time.

However, the concentration measured by the light scattering detection method is not a mass concentration, but a number concentration corresponding to the number of particles per unit volume. A number concentration of particles contained in a gas has been converted into a mass concentration by multiplying the number concentration by a predetermined conversion factor. However, the conversion accuracy is not high when this method is used. The inventors have succeeded in improving the conversion accuracy by defining a conversion factor by a function of humidity. The success in improving the conversion accuracy may relate to the phenomenon that when the humidity of a gas changes, the distribution of particle size and the physical-chemical properties of particles change because the moisture absorption amount of the particles changes. Particles are a mixture of various components. The hygroscopicity of particles depends on the composition of the particles. For example, when particles are composed of ammonium sulfate, the light-scattering cross-section at a humidity of 90% is five times greater than the light-scattering cross-section under arid conditions. When particles are composed of organic substances, the light-scattering cross-section is less affected by the humidity. As described, as the composition of particles changes, the hygroscopicity of the particles changes. The composition of particles changes depending on a location and a time. Thus, if the same function is used as a function for converting a number concentration into a mass concentration, the conversion accuracy from the number concentration into the mass concentration cannot be increased. Thus, the inventors thought about using an appropriate function in accordance with the change in composition of particles.

As described above, it is difficult to install many measurement stations with high measurement accuracy. The following embodiments install measurement stations equipped with a mass concentration detector, which can measure precisely but is costly, and measurement stations equipped with a number concentration detector, which is less costly but measures less precisely, to allow for the installation of many measurement stations.

First Embodiment

FIG. 1 is a block diagram of a system that employs a calculation device and a calculation program in accordance with a first embodiment. As illustrated in FIG. 1, a system 100 includes measurement stations 20, 22, and 22*a*, and a computer 10. The measurement station 20 doubles as measurement stations 24 and 26. The measurement stations 24 and 26 are installed in approximately the same location. The measurement station 24 includes a mass concentration measuring instrument 30. The measurement station 26 includes a number concentration measuring instrument 32 and a hygrometer 34. The measurement stations 22 and 22*a* are installed in a location different from the location where the measurement station 20 is installed. Each of the measurement stations 22 and 22*a* includes the number concentration measuring instrument 32 and the hygrometer 34, but does not include the mass concentration measuring instrument 30. The measurement stations 20 and 22 are coupled to the computer 10 through a wired Internet network 36. The measurement station 22*a* is coupled to the computer 10 through a wireless network 38 such as a mobile communication network. Various communication methods including wired communication networks and wireless communication networks can be appropriately used to transmit and receive data between the measurement stations 20, 22, and 22*a* and the computer 10.

The mass concentration measuring instrument 30 employs, for example, the beta attenuation measurement, and measures a mass concentration Cm0 of particles such as $PM_{2.5}$ contained in a gas (e.g., the air) in the measurement station 24. The number concentration measuring instrument 32 employs, for example, the light scattering detection method, and measures a number concentration Cn0 of the particles such as $PM_{2.5}$ contained in the gas in the measurement station 24. The hygrometer 34 measures a relative humidity h0 of the gas in the measurement station 24. The computer 10 is, for example, a server computer. The computer 10 is a calculation device, and executes a calculation program and a calculation method.

Figure 2:
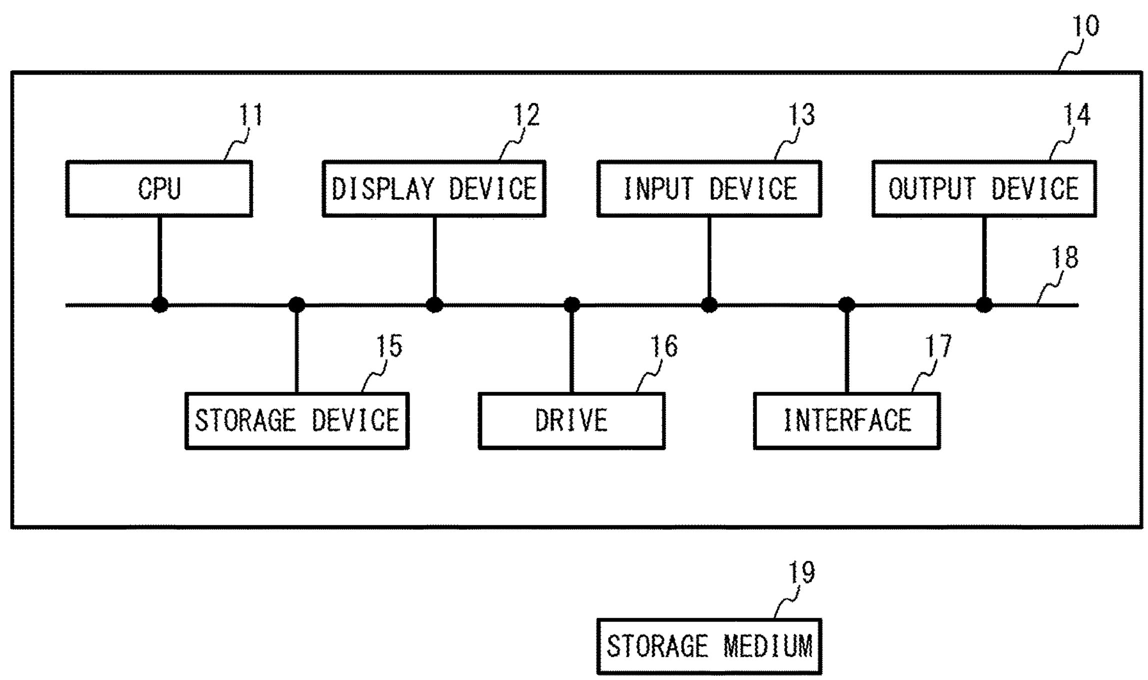
FIG. 2 is a block diagram of a computer functioning as the calculation device of the first embodiment.

FIG. 2 is a block diagram of the computer functioning as a calculation device in accordance with the first embodiment. The computer 10 includes a Central Processing Unit (CPU) 11, a display device 12, an input device 13, an output device 14, a storage device 15, a storage medium drive 16, a communication interface 17, and an internal bus 18. The display device 12 includes a display panel such as, for example, a liquid crystal panel, and displays commands, data, or the like. Examples of the input device 13 are, but are not limited to, a keyboard, a mouse, and a touch panel. The input device 13 is used to input commands, data, or the like. The output device 14 is, for example, a printer, and outputs commands, data, or the like. The storage device 15 is, for example, a volatile memory such as a Random Access Memory (RAM) or a nonvolatile memory such as a flash memory or a hard disk drive, and stores programs and data during processing or after processing. The storage medium drive 16 is used to install a program stored in a storage medium 19. The communication interface 17 obtains data such as mass concentrations, number concentrations, and humidities from the measurement stations 20, 22, and 22*a*. The internal bus 18 interconnects the devices in the computer 10.

A portable storage medium may be used as the storage medium 19 that stores a program and can be read by the computer 10. Examples of the portable storage medium include, but are not limited to, a Compact Disc Read Only Memory (CD-ROM) disc, a Digital Versatile Disc (DVD), a Blu-ray Disc, and a Universal Serial Bus (USB). A flash memory or a Hard Disk Drive (HDD) may be used as the storage medium 19.

Figure 3:
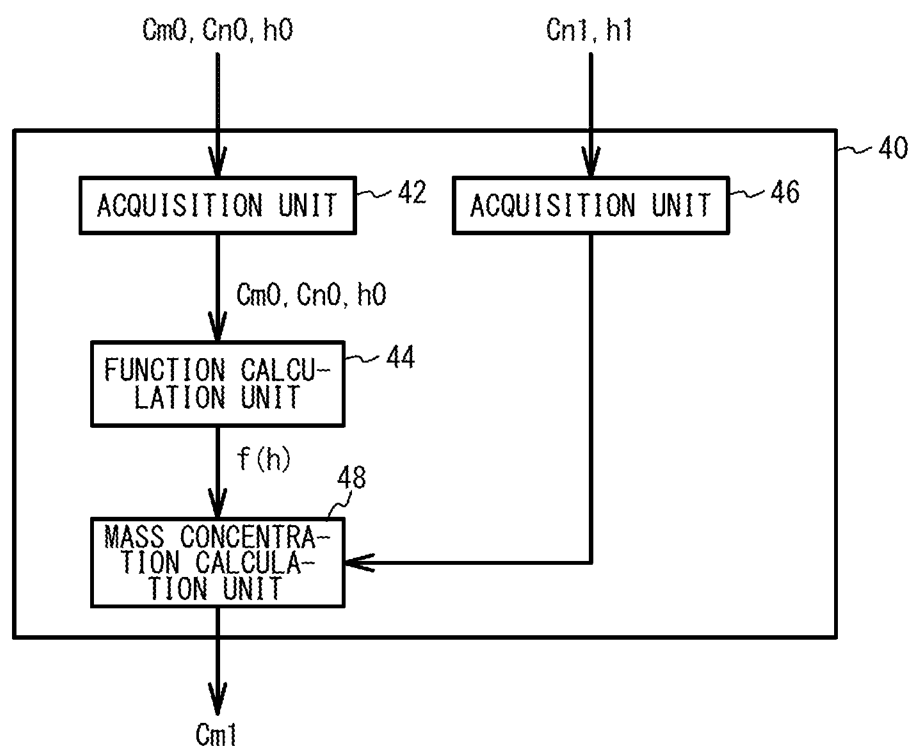
FIG. 3 is a functional block diagram of the calculation device of the first embodiment.
Figure 4:
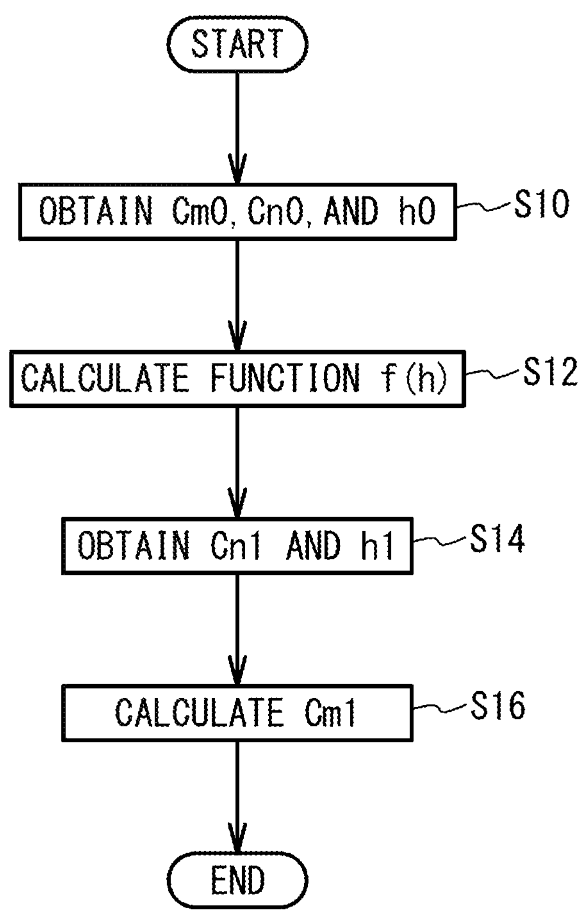
FIG. 4 is a flowchart of processes executed by the computer in the first embodiment.

FIG. 3 is a functional block diagram of a calculation device 40 in accordance with the first embodiment. The computer 10 functions as illustrated in FIG. 3 by the cooperation between the hardware components illustrated in FIG. 2 and software. FIG. 4 is a flowchart of processes executed by the computer in the first embodiment.

As illustrated in FIG. 3 and FIG. 4, an acquisition unit 42 obtains, from the measurement station 24, the mass concentration Cm0 measured in the measurement station 24. The acquisition unit 42 obtains, from the measurement station 26, the number concentration Cn0 and the humidity h0 measured in the measurement station 26 (step S10). A function calculation unit 44 calculates a function f(h) defining a relationship of a mass concentration Cm and a number concentration Cn to a humidity h based on the obtained mass concentrations Cm0, the obtained number concentrations Cn0, and the obtained humidities h0 (step S12). For example, the function f(h) is Cn/Cm with respect to the relative humidity h. An acquisition unit 46 obtains, from the measurement stations 22 and 22*a*, number concentrations Cn1 and humidities h1 measured in the measurement stations 22 and 22*a* (step S14). A mass concentration calculation unit 48 calculates the mass concentration Cm1 of particles contained in a gas in each of the measurement stations 22 and 22*a* from the obtained number concentration Cn1 and the obtained humidity h1 based on the function f(h) (step S16). For example, Cm1 is calculated by the equation: Cm1=Cn/f(h).

Figure 5:
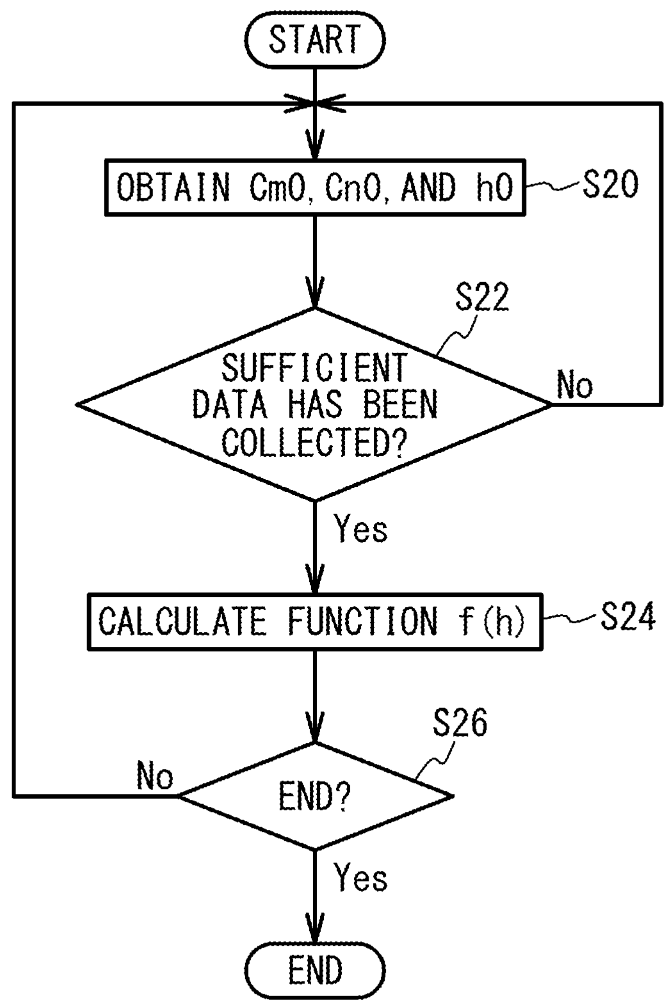
FIG. 5 is a flowchart illustrating a method of calculating a function in the first embodiment.

FIG. 5 is a flowchart illustrating a method of calculating the function in the first embodiment. As illustrated in FIG. 5, the acquisition unit 42 obtains the mass concentration Cm0, the number concentration Cn0, and the humidity h0 (step S20). For example, the acquisition unit 42 obtains the mass concentration Cm0 at regular intervals (for example, at one-hour intervals), and obtains the number concentration Cn0 and the humidity h0 at intervals shorter than the intervals at which the mass concentration Cm0 is obtained (for example, at one-minute intervals). The acquisition unit 42 stores the mass concentration Cm0, the number concentration Cn0, and the humidity h0 measured at approximately the same time, together as a set, in a storage unit such as the storage device 15 illustrated in FIG. 2. When the mass concentration Cm0 is measured at intervals different from the intervals at which the number concentration Cn0 and the humidity h0 are measured, the number concentration Cn0 and the humidity h0 measured at a time closest to the time at which the mass concentration Cm0 was measured may be stored together with the mass concentration Cm0 as a set of the mass concentration Cm0, the number concentration Cn0, and the humidity h0 measured at approximately the same time. Alternatively, a plurality of number concentrations Cn0 and a plurality of humidities h0 measured during the measurement period from when the measurement of the mass concentration Cm0 is started till when the next measurement of the mass concentration Cm0 is started may be stored together with the last-measured mass concentration Cm0 as sets of the mass concentration Cm0, the number concentration Cn0, and the humidity h0 measured at approximately the same time. Alternatively, the average of a plurality of number concentrations Cn0 and the average of a plurality of humidities h0 measured during the measurement period may be stored together with the last-measured mass concentration Cm as a set of the mass concentration Cm0, the number concentration Cn0, and the humidity h0 measured at approximately the same time.

The function calculation unit 44 determines whether data sufficient to calculate the function has been collected (step S22). When the determination is No, the process returns to step S20. When the determination is Yes, the function calculation unit 44 calculates the function from the collected mass concentrations Cm0 and the collected number concentrations Cn0 (step S24). The details will be described later. The function calculation unit 44 stores the function f(h) in a storage unit such as the storage device 15. The function f(h) is stored as, for example, a table of Cn/Cm versus humidity h in a storage unit. The function calculation unit 44 determines whether the process ends (step S26). For example, when the concentration measurement is stopped, the determination becomes Yes. When the determination is Yes, the process ends. When the determination is No, the process returns to step S20.

Figure 6:
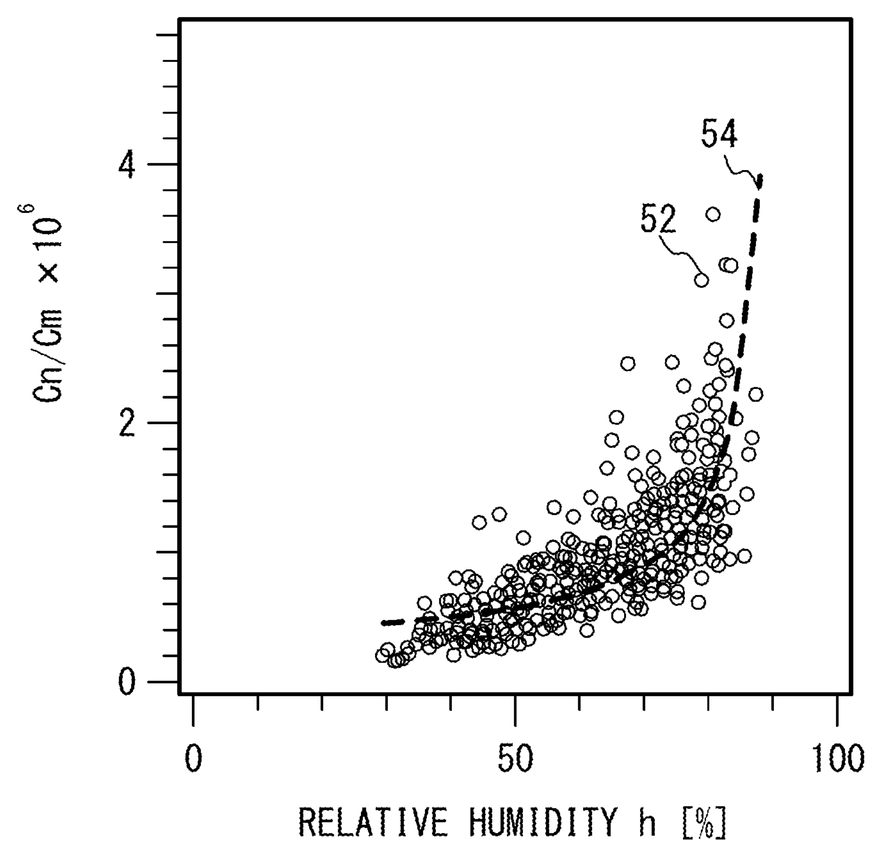
FIG. 6 is a graph of a ratio of a number concentration to a mass concentration versus relative humidity in the first embodiment.

FIG. 6 is a graph of a ratio of a number concentration to a mass concentration versus relative humidity in the first embodiment. As illustrated in FIG. 6, the function calculation unit 44 calculates Cn/Cm from the mass concentrations Cm1 and the number concentrations Cn1 measured at approximately the same time in the measurement stations 24 and 26. Dots 52 represent Cn/Cm with respect to the humidity h1 measured at approximately the same time. Since the humidity h changes depending on the environment of the measurement stations 24 and 26, the dots 52 of Cn/Cm with respect to various humidities h are obtained. The function calculation unit 44 calculates an approximate curve 54 from the dots 52 with use of an approximate equation. The function calculation unit 44 defines the function of the approximate curve 54 as the function f(h).

The function calculation unit 44 can calculate the function f(h) with use of the mass concentrations Cm0, the number concentrations Cn0, and the humidities h0 measured during a predetermined period of time (for example, for one month or one week) or an inconstant period of time. Alternatively, the function calculation unit 44 can calculate the function f(h) with use of the mass concentrations Cm0, the number concentrations Cn0, and the humidities h0 measured during the latest predetermined period of time (for example, one month or one week) or the latest inconstant period of time.

At step S16 in FIG. 4, the mass concentration calculation unit 48 calculates the mass concentration Cm1 with use of the latest function f(h).

As described in the first embodiment, the acquisition unit 42 (an acquisition unit) obtains the mass concentration Cm0 in the measurement station 24 (a first measurement station) and the number concentration Cn0 and the humidity h in the measurement station 26 (a second measurement station) as at step S10 in FIG. 4. As at step S12, the function calculation unit 44 (a calculation unit) calculates the function f(h) that defines a relationship of the mass concentration Cm and the number concentration Cn to the humidity h based on the mass concentrations Cm0, the number concentrations Cn0, and the humidities h. As at step S16, the function f(h) is a function for calculating the mass concentration Cm1 of particles contained in a gas in each of the measurement stations 22 and 22*a* from the number concentration Cn1 and the humidity h1 measured in each of the measurement stations 22 and 22*a* (third measurement stations).

For example, in a certain area, the compositions of particles in the measurement stations 24, 26, 22, and 22*a* are considered the same. The ratios of the mass concentration to the number concentration in the measurement stations 24, 26, 22, and 22*a* are approximately the same. Thus, the function f(h) is calculated from the mass concentration Cm0 measured in the measurement station 24 and the number concentration Cn0 and the humidity h0 measured in the measurement station 26. The use of the function f(h) allows the mass concentration Cm1 in each of the measurement stations 22 and 22*a* to be precisely calculated from the number concentration Cn1 and the humidity h1 measured in each of the measurement stations 22 and 22*a*. The measurement stations 22 and 22*a* do not include the mass concentration measuring instrument 30. Thus, many measurement stations 22 and 22*a* can be installed. Additionally, the measurement stations 22 and 22*a* can measure the number concentration Cn1 and the humidity h1 at short intervals. Thus, the mass concentrations Cm1 in the measurement stations 22 and 22*a* can be calculated in real time.

In addition, as illustrated in FIG. 1, the measurement station 24 and the measurement station 26 are located in the same location. Thus, the mass concentration Cm0, the number concentration Cn0, and the humidity h0 in approximately the same location can be measured. Accordingly, the function f(h) is calculated more precisely. The case where the measurement stations 24 and 26 are located in the same location is, for example, a case where the measurement stations 24 and 26 are located in the same building or in the same premise, or a case where the distance between the measurement stations 24 and 26 is approximately 100 m or less. The case where the measurement stations 24 and 26 are located in different locations is a case where the distance between the measurement stations 24 and 26 is, for example, several hundred meters or greater.

As at steps S20 and S22 in FIG. 5, the acquisition unit 42 obtains a plurality of mass concentrations Cm0 in the measurement station 24 measured at regular or odd intervals and a plurality of number concentrations Cn0 and a plurality of humidities h0 in the measurement station 26 measured at regular or odd intervals. At step S24, the function calculation unit 44 calculates the function f(h) at regular or odd intervals. Accordingly, at step S16 of FIG. 4, the mass concentration calculation unit 48 can calculate the mass concentrations Cm1 in the measurement stations 22 and 22*a* with use of the latest function f(h) among the functions calculated at regular or odd intervals. Therefore, even when the composition of particles changes in accordance with the change in environment or seasonal variation, the mass concentration can be calculated precisely.

As described at step S20 of FIG. 5 and in FIG. 6, the acquisition unit 42 obtains a plurality of mass concentrations Cm0 measured in the measurement station 24 for a predetermined period of time and a plurality of number concentrations Cn0 and a plurality of humidities h0 measured in the measurement station 26 for a predetermined period of time. The function calculation unit 44 calculates the function f(h) based on the plurality of mass concentrations Cm0, the plurality of number concentrations Cn0, and the plurality of humidities h0. Accordingly, the function f(h) can be calculated.

As illustrated in FIG. 6, the function f(h) is preferably a ratio Cn/Cm of the number concentration Cn to the mass concentration Cm varying as a function of the humidity h. This eases the calculation of the function f(h). The function f(h) may be, other than Cn/Cm, a function containing Cn and Cm and varying as a function of a humidity.

Second Embodiment

Figure 7:
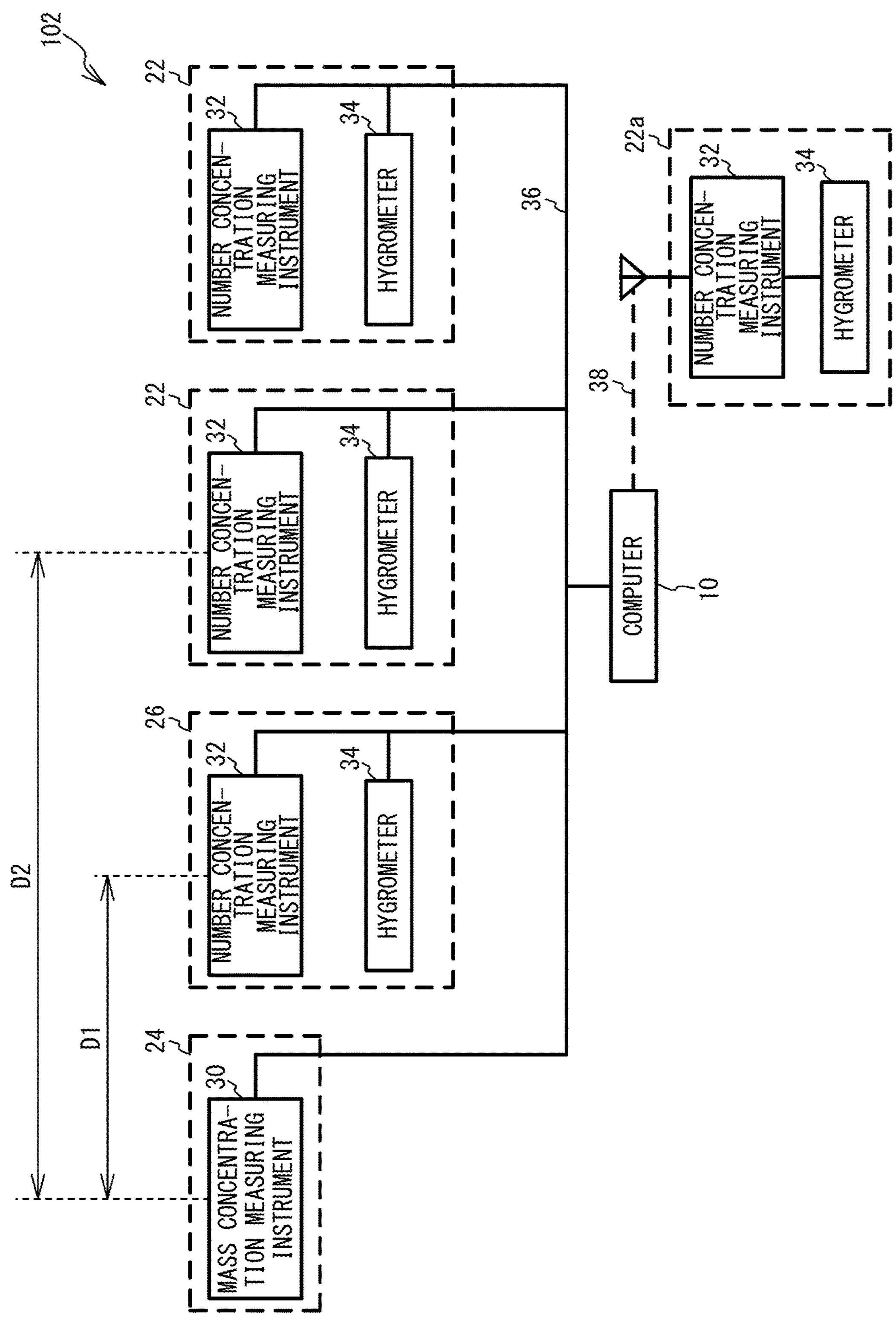
FIG. 7 is a block diagram of a system that employs a calculation device and a calculation program in accordance with a second embodiment.

FIG. 7 is a block diagram of a system that employs a calculation device and a calculation program in accordance with a second embodiment. As illustrated in FIG. 7, in a system 102, the measurement station 24 and the measurement station 26 are installed in different locations. The distance between the measurement stations 24 and 26 is a distance D1. The distance between the measurement station closest to the measurement station 24 among the measurement stations 22 and 22*a* and the measurement station 24 is a distance D2. Other configurations are the same as those of the first embodiment, and thus the description is omitted.

In the second embodiment, the distance D1 is less than the distance D2. This configuration allows for the measurement of the mass concentrations Cm0, the number concentrations Cn0, and the humidities h0 in relatively close locations. Thus, the function f(h) can be calculated more precisely. The distance D1 can be, for example, 1 km or less.

Third Embodiment

Figure 8:
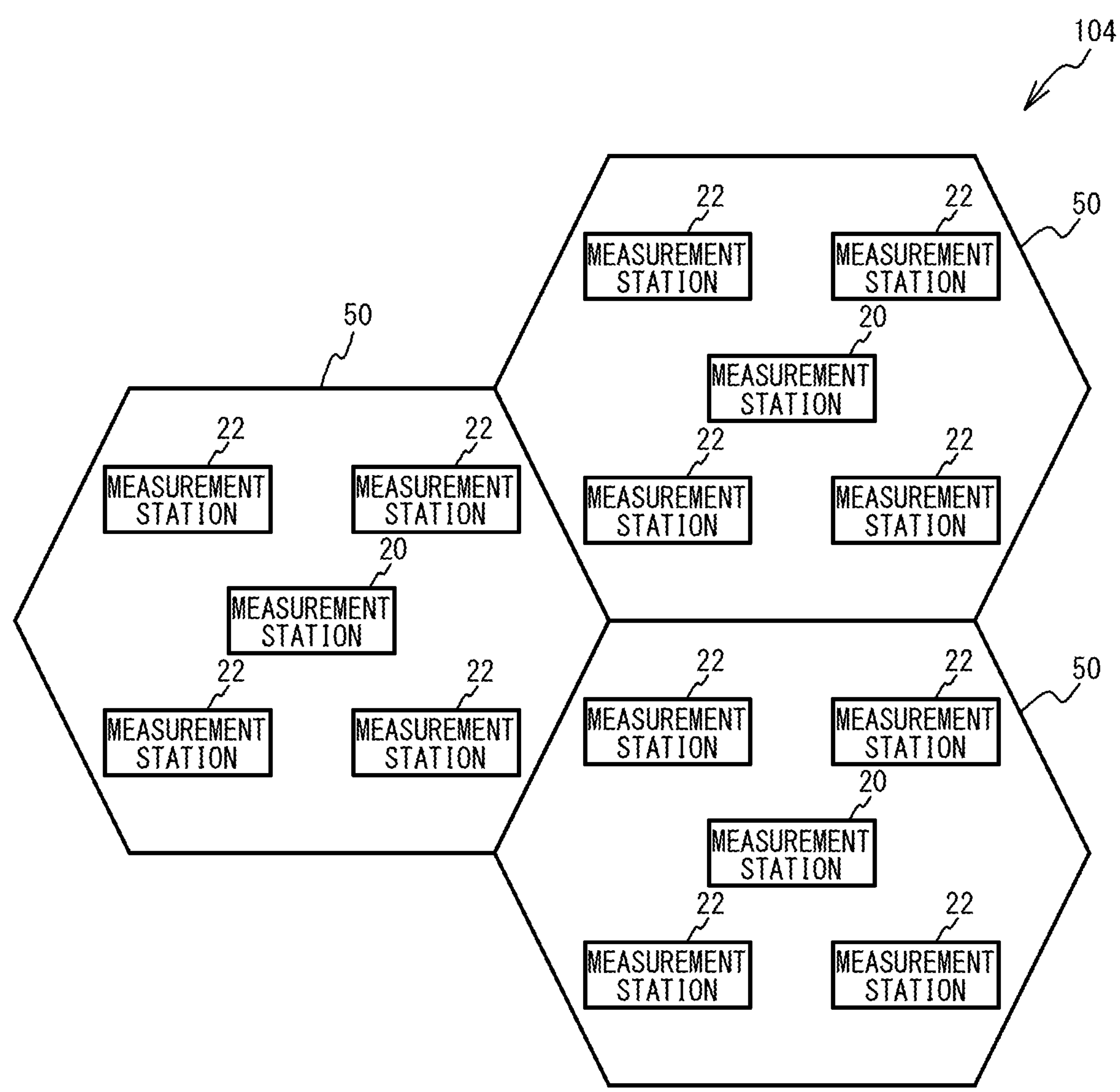
FIG. 8 is a block diagram of a system that employs a calculation device and a calculation program in accordance with a third embodiment.

FIG. 8 is a block diagram of a system that employs a calculation device and a calculation program in accordance with a third embodiment. As illustrated in FIG. 8, in a system 104, an area is divided into a plurality of cells 50. The measurement station 20 and a plurality of the measurement stations 22 are installed in each cell 50. As in the first embodiment, the measurement station 20 includes the measurement stations 24 and 26. As in the second embodiment, the measurement stations 24 and 26 may be provided instead of the measurement station 20. Other configurations are the same as those of the first embodiment, and thus the description is omitted.

In the third embodiment, the measurement station 20 and the measurement stations 22 are installed in each of the cells 50. The function calculation unit 44 calculates the mass concentration Cm1 in the measurement station 22 based on the mass concentration Cm0, the number concentration Cn0, and the humidity h0 in the measurement station 20 in the same cell 50. The division of an area into a plurality of cells 50 allows for more precise calculation of the function f(h), and more precise calculation of the mass concentration Cm1.

Fourth Embodiment

Figure 9:
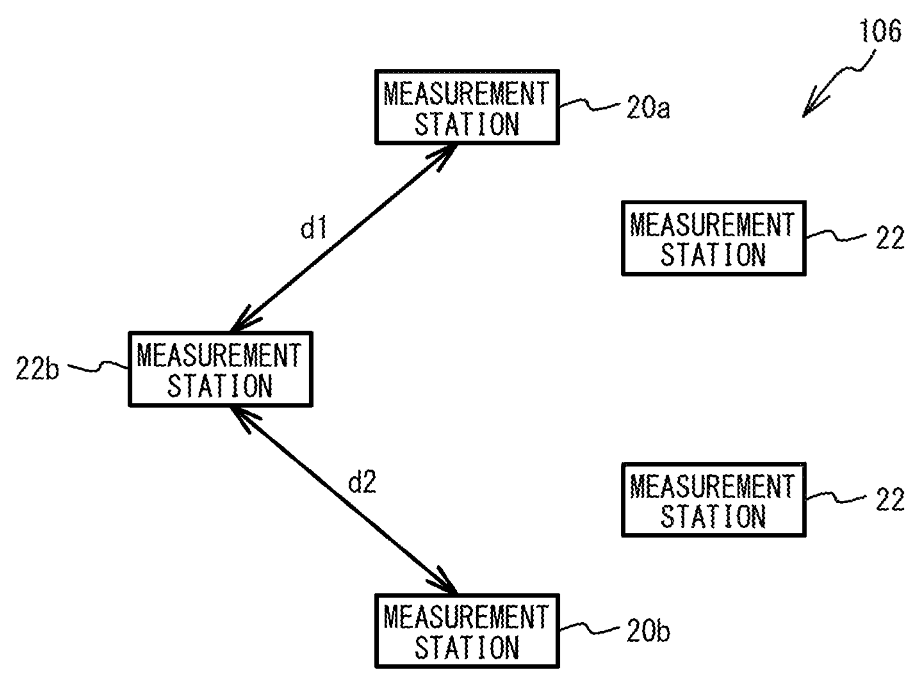
FIG. 9 is a block diagram of a system that employs a calculation device and a calculation program in accordance with a fourth embodiment.

FIG. 9 is a block diagram of a system that employs a calculation device and a calculation program in accordance with a fourth embodiment. As illustrated in FIG. 9, in a system 106, the measurement stations 20*a* and 20*b* of the measurement stations 20 are installed. The distance between a measurement station 22*b* out of the measurement stations 22 and the measurement station 20*a* is d1, and the distance between the measurement station 22*b* and the measurement station 20*b* is d2. As in the first embodiment, each of the measurement stations 20*a* and 20*b* includes the measurement stations 24 and 26. As in the second embodiment, the measurement stations 24 and 26 may be provided instead of the measurement stations 20*a* and 20*b*.

At step S10 in FIG. 4, the acquisition unit 42 obtains the mass concentration Cm0, the number concentration Cn0, and the humidity h0 in each of the measurement stations 20*a* and 20*b*. At step S12, the function calculation unit 44 calculates a function $f1(h)$ relative to the measurement station 20*a* and a function $f2(h)$ relative to the measurement station 20*b*. The function calculation unit 44 calculates the function f(h) for calculating the mass concentration Cm1 in the measurement station 22*b* based on the functions $f1(h)$ and $f2(h)$. The function calculation unit 44 calculates the function f(h) with use of, for example, the following equation.

$$f(h)=d2/(d1+d2)\times f1(h)+d1/(d1+d2)\times f2(h)$$

Other configurations are the same as those of the first embodiment, and thus the description is omitted.

The fourth embodiment configures the function calculation unit 44 to calculate the function f(h) based on the mass concentrations Cm0, the number concentrations Cn0, and the humidities h0 in the measurement stations 20*a* and 20*b* and the distances d1 and d2. This configuration allows the mass concentration Cm1 in the measurement station 22*b* to be calculated more precisely.

Furthermore, at step S12, the function calculation unit 44 may weight the distances d1 and d2 based on information on the environment of at least one of the measurement stations 20*a* and 20*b* and the measurement station 22*b* to calculate the function f(h) in the measurement station 22*b*. This configuration allows the mass concentration Cm1 in the measurement station 22*b* to be calculated more precisely.

The function calculation unit 44 calculates the function f(h) with use of, for example, the following equation.

$$f(h)=w1\times d2/(d1+d2)\times f1(h)+w2\times d1/(d1+d2)\times f2(h)$$

Here, w1 and w2 are weighting factors meeting the following relation: w1+w2=1. The information on the environment may be information on weather such as wind direction. For example, when the measurement station 20*a* is located further upwind than the measurement station 22*b*, and the measurement station 20*b* is located further downwind than the measurement station 22*b*, w1 is configured to be less than w2 (w1<w2).

Fifth Embodiment

Particles such as $PM_{2.5}$ are composed of various components such as, for example, elemental carbon, organic substances, and inorganic salts. If the composition of particles is identified, the information on the source of the particles can be obtained. However, the composition analysis of particles requires an expensive device. Thus, it is difficult to easily analyze the composition of particles.

Figure 10:
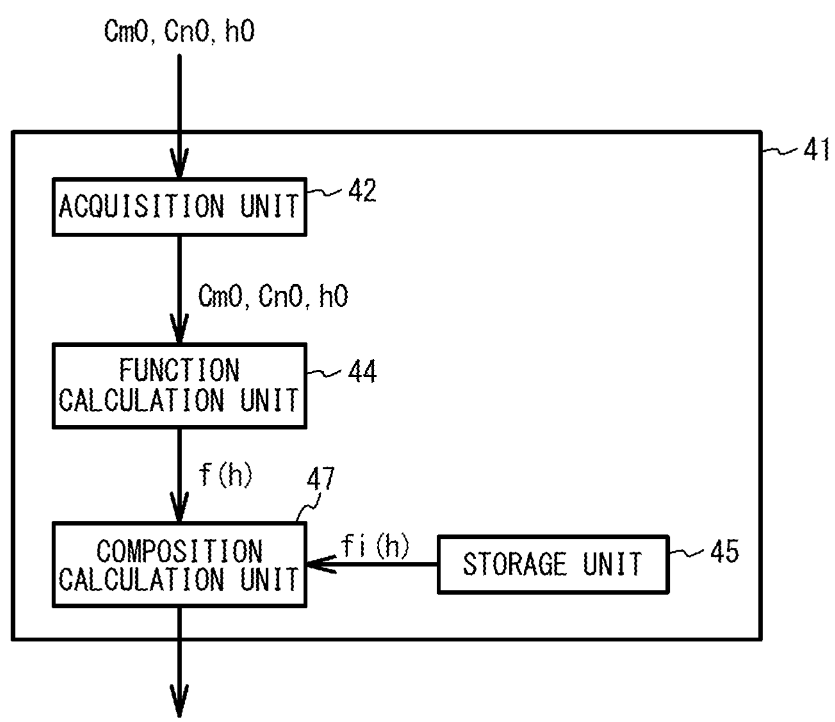
FIG. 10 is a functional block diagram of a calculation device in accordance with a fifth embodiment.
Figure 11:
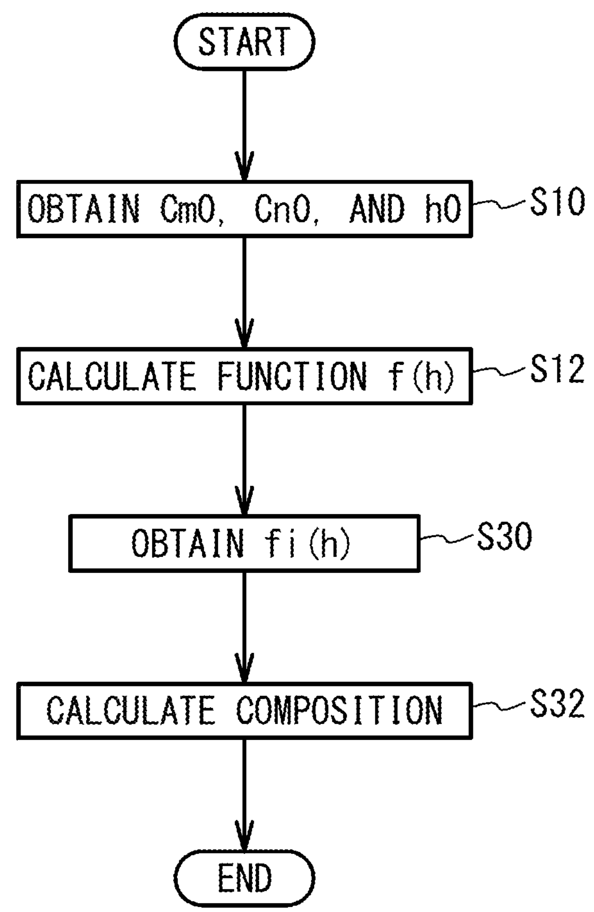
FIG. 11 is a flowchart of processes executed by a computer in the fifth embodiment.

In a fifth embodiment, the computer 10 illustrated in FIG. 2 functions as a calculation device, and executes a calculation program. FIG. 10 is a functional block diagram of a calculation device 41 in accordance with the fifth embodiment. The computer 10 functions as illustrated in FIG. 10 by the cooperation between the hardware components illustrated in FIG. 2 and software. FIG. 11 is a flowchart of processes executed by the computer in the fifth embodiment.

As illustrated in FIG. 10 and FIG. 11, the acquisition unit 42 obtains the mass concentration Cm0 from the measurement station 24 as in the first embodiment. The acquisition unit 42 obtains the number concentration Cn0 and the humidity h0 from the measurement station 26 (step S10). The function calculation unit 44 calculates the function f(h) based on the obtained mass concentrations Cm0, the obtained number concentrations Cn0, and the obtained humidities h0 (step S12). A composition calculation unit 47 obtains functions fi(h) each corresponding to a constituent from a storage unit 45 such as the storage device 15 (step S30). The function fi(h) is a function defining a relationship of Cn/Cm to the humidity h when particles are composed of a single constituent. The function fi(h) corresponding to each constituent is measured in advance, and stored in the storage unit 45. The composition calculation unit 47 calculates the composition of particles based on the functions f(h) and fi(h) (step S32). The process ends after step S32.

Figure 12A:
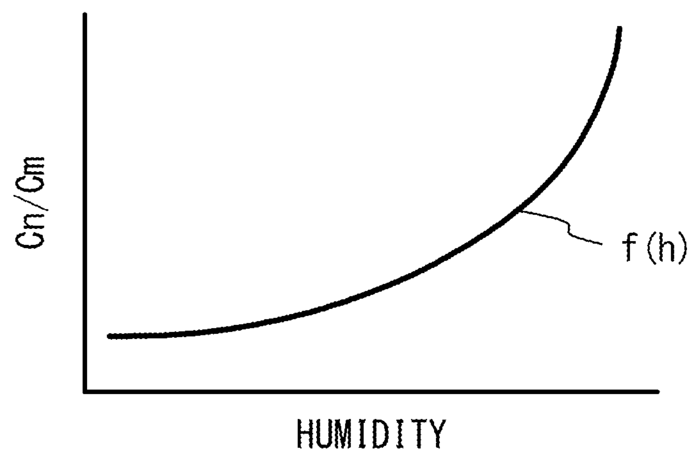
FIG. 12A through FIG. 12C illustrate functions f(h) and fi(h) in the fifth embodiment.
Figure 12B:
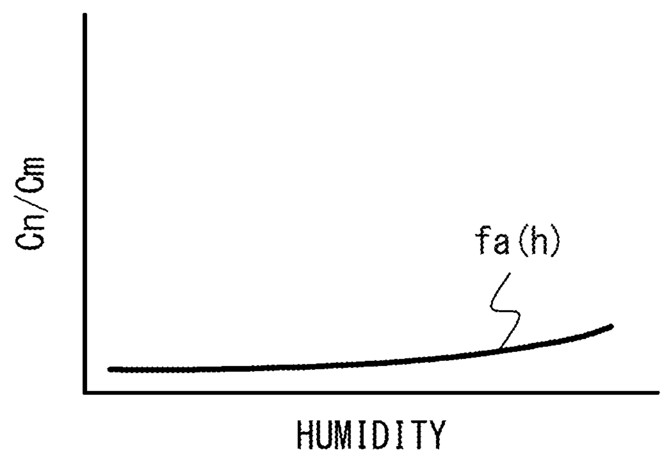
Figure 12C:
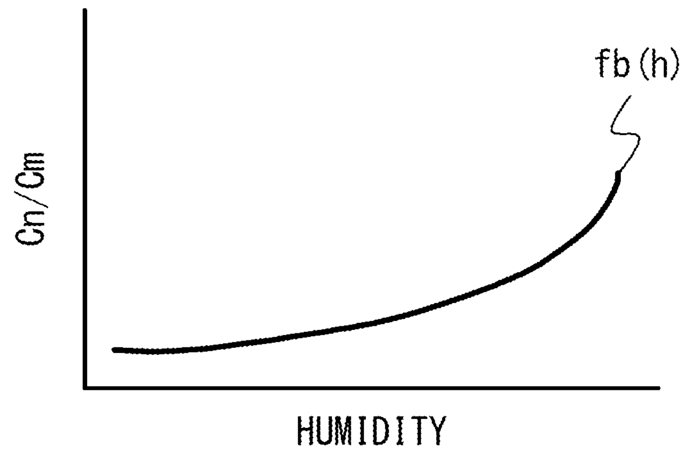

FIG. 12A through FIG. 12C illustrate the functions f(h) and fi(h) in the fifth embodiment. FIG. 12A illustrates the function f(h) calculated by the function calculation unit 44. FIG. 12B illustrates a function fa(h) of a constituent A stored in the storage unit 45. FIG. 12C illustrates a function fb(h) of a constituent B stored in the storage unit 45. The composition calculation unit 47 calculates the approximate equation that best approximates the function f(h) by linearly combining the functions fi(h). For example, when f(h) is approximated by the equation $x \times fa(h) + y \times fb(h)$, the constituents A and B exist in particles in the proportion of x to y.

The fifth embodiment preliminarily sets the function fi(h) defining a relationship of the mass concentration Cm and the number concentration Cn to the humidity h in association with each constituent of particles. The composition calculation unit 47 (a calculation unit) calculates the composition of particles contained in a gas in the measurement station 24 based on the function f(h) and a plurality of functions fi(h). Accordingly, the composition of particles can be easily identified.

The function f(h) and the functions fi(h) are preferably ratios Cn/Cm of the number concentration Cn to the mass concentration Cm varying as a function of the humidity h. This eases the calculation of the functions f(h) and fi(h). The functions f(h) and fi(h) may be, other than Cn/Cm, a function containing Cn and Cm and varying as a function of a humidity.

The composition calculation unit 47 preferably calculates the composition based on the factors x and y of the linear combination when the function f(h) is represented by the linear combination of the functions fi(h). This eases the calculation of the composition of particles.

The calculation devices of the first through fourth embodiments may calculate the composition of particles as in the fifth embodiment. The calculation device of the fifth embodiment may be provided separately from the calculation devices of the first through fourth embodiments.

There may be provided a calculation device including: an acquisition unit configured to obtain a mass concentration of particles contained in a gas measured in a first measurement station, a number concentration of particles contained in the gas measured in a second measurement station, and a humidity of the gas measured in the second measurement station; and a calculation unit configured to calculate a function, which defines a relationship of a mass concentration and a number concentration to a humidity, based on the mass concentration in the first measurement station, the number concentration and the humidity in the second measurement station obtained by the acquisition unit, and to calculate a composition of the particles contained in the gas in at least one of the first measurement station and the second measurement station based on the function and a plurality of functions each defining a relation of a mass concentration and a number concentration to a humidity and being preliminarily set so as to correspond to each constituent of particles.

There may be provided a computer-readable non-transitory storage medium storing a calculation program causing a computer to execute a process, the process including: obtaining a mass concentration of particles contained in a gas measured in a first measurement station, a number concentration of particles contained in the gas measured in a second measurement station, and a humidity of the gas measured in the second measurement station; calculating a function, which defines a relationship of a mass concentration and a number concentration to a humidity, based on the mass concentration in the first measurement station, the number concentration and the humidity in the second measurement station obtained in the obtaining; and calculating a composition of the particles contained in the gas in at least one of the first measurement station and the second measurement station based on the function and a plurality of functions each defining a relation of a mass concentration and a number concentration to a humidity and being preliminarily set so as to correspond to each constituent of particles.

There may be provided a calculation method executed in a computer, the calculation method including: obtaining a mass concentration of particles contained in a gas measured in a first measurement station, a number concentration of particles contained in the gas measured in a second measurement station, and a humidity of the gas measured in the second measurement station; calculating a function, which defines a relationship of a mass concentration and a number concentration to a humidity, based on the mass concentration in the first measurement station, the number concentration and the humidity in the second measurement station obtained in the obtaining; and calculating a composition of the particles contained in the gas in at least one of the first measurement station and the second measurement station based on the function and a plurality of functions each defining a relation of a mass concentration and a number concentration to a humidity and being preliminarily set so as to correspond to each constituent of particles.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various change, substitutions, and alterations could be made hereto without departing from the spirit and scope of the invention.

What is claimed is:

1. A calculation device comprising:

a memory; and a processor coupled to the memory and configured to:

obtain a mass concentration of particles contained in a gas measured in a first measurement station, a number concentration of particles contained in the gas measured in a second measurement station, and a humidity of the gas measured in the second measurement station; and calculate a function, which defines a relationship of a mass concentration and a number concentration to a humidity and is used to calculate a mass concentration of particles contained in the gas in a third measurement station from a number concentration of particles contained in the gas and a humidity of the gas measured in the third measurement station, based on the mass concentration in the first measurement station and the number concentration and the humidity in the second measurement station obtained by the acquisition unit, the third measurement station being installed in a location different from a location where the first measurement station and the second measurement station are installed, wherein the processor is configured to obtain a plurality of the mass concentrations measured in the first measurement station for a predetermined period of time and a plurality of the number concentrations and a plurality of the humidities measured in the second measurement station for the predetermined period of time, and calculate the function based on the plurality of the mass concentrations, the plurality of the number concentrations, and the plurality of the humidities.

2. The calculation device of claim 1, wherein the first measurement station and the second measurement station are located in a same location.

3. The calculation device of claim 1, wherein the first measurement station and the second measurement station are located in different locations, and a distance between the first measurement station and the second measurement station is less than a distance between the first measurement station and the third measurement station.

4. The calculation device of claim 1, wherein the processor is configured to obtain the plurality of the mass concentrations in the first measurement station measured at regular or odd intervals and a plurality of the number concentrations and the plurality of the humidities in the second measurement station measured at regular or odd intervals, and calculate the function at regular or odd intervals.

5. The calculation device of claim 1, wherein the first measurement station, the second measurement station, and the third measurement station are installed in each of a plurality of cells, and the processor is configured to calculate the mass concentration in the third measurement station based on the mass concentration in the first measurement station in one of the plurality of cells and the number concentration and the humidity in the second measurement station in the one of the plurality of cell.

6. The calculation device of claim 1, wherein the processor is configured to obtain the mass concentration in each of a plurality of the first measurement stations, and the number concentration and the humidity in each of a plurality of the second measurement stations, and calculate the function based on the mass concentration in each of the plurality of the first measurement stations, the number concentration and the humidity in each of the plurality of the second measurement stations, and distances between the plurality of the second measurement stations and the third measurement station.

7. The calculation device of claim 6, wherein the processor is configured to weight the distances based on information on an environment of at least one of the plurality of the first measurement stations, the plurality of the second measurement stations, and the third measurement station to calculate the function.

8. The calculation device of claim 1, wherein the processor is configured to calculate a composition of the particles contained in the gas in the first measurement station based on the function and a plurality of functions each defining a relation of a mass concentration and a number concentration to a humidity and being preliminarily set so as to correspond to each constituent of particles.

9. The calculation device of claim 8, wherein each of the function and the plurality of functions is a ratio of a number concentration to a mass concentration varying as a function of a humidity.

10. The calculation device of claim 9, wherein the processor is configured to calculate the composition based on a factor of a linear combination when the function is represented by the linear combination of the plurality of functions.

11. The calculation device of claim 1, wherein the processor is configured to calculate the mass concentration of particles contained in the gas in the third measurement station from the number concentration of particles contained in the gas measured in the third measurement station based on the function.

12. The calculation device of claim 1, wherein the function is a ratio of a number concentration to a mass concentration varying as a function of a humidity.

13. A computer-readable non-transitory storage medium storing a calculation program causing a computer to execute a process, the process comprising:

obtaining a mass concentration of particles contained in a gas measured in a first measurement station, a number concentration of particles contained in the gas measured in a second measurement station, and a humidity of the gas measured in the second measurement station; and calculating a function, which defines a relationship of a mass concentration and a number concentration to a humidity and is used to calculate a mass concentration of particles contained in the gas in a third measurement station from a number concentration of particles contained in the gas and a humidity of the gas measured in the third measurement station, based on the mass concentration in the first measurement station and the number concentration and the humidity in the second measurement station obtained in the obtaining, the third measurement station being installed in a location different from a location where the first measurement station and the second measurement station are installed, wherein:

the obtaining includes obtaining a plurality of the mass concentrations measured in the first measurement station for a predetermined period of time and a plurality of the number concentrations and a plurality of the humidities measured in the second measurement station for the predetermined period of time; and the calculating includes calculating the function based on the plurality of the mass concentrations, the plurality of the number concentrations, and the plurality of the humidities.

14. A calculation method executed in a computer, the calculation method comprising:

obtaining a mass concentration of particles contained in a gas measured in a first measurement station, a number concentration of particles contained in the gas measured in a second measurement station, and a humidity of the gas measured in the second measurement station; and calculating a function, which defines a relationship of a mass concentration and a number concentration to a humidity and is used to calculate a mass concentration of particles contained in the gas in a third measurement station from a number concentration of particles contained in the gas and a humidity of the gas measured in the third measurement station, based on the mass concentration in the first measurement station and the number concentration and the humidity in the second measurement station obtained in the obtaining, the third measurement station being installed in a location different from a location where the first measurement station and the second measurement station are installed, wherein:

the obtaining includes obtaining a plurality of the mass concentrations measured in the first measurement station for a predetermined period of time and a plurality of the number concentrations and a plurality of the humidities measured in the second measurement station for the predetermined period of time; and the calculating includes calculating the function based on the plurality of the mass concentrations, the plurality of the number concentrations, and the plurality of the humidities.

* * * * *